US006410668B1

(12) United States Patent
Chiari

(10) Patent No.: US 6,410,668 B1
(45) Date of Patent: Jun. 25, 2002

(54) ROBUST POLYMER COATING

(76) Inventor: Marcella Chiari, V. Gian Battisla Brocchi, 11, Milan (IT), 20131

( * ) Notice: Subject to any disclaimer, the term of this patent is extended or adjusted under 35 U.S.C. 154(b) by 0 days.

(21) Appl. No.: 09/637,226

(22) Filed: Aug. 11, 2000

Related U.S. Application Data
(60) Provisional application No. 60/150,167, filed on Aug. 21, 1999.

(51) Int. Cl.$^7$ .............................................. C08F 16/04
(52) U.S. Cl. ................................................ 526/238.23
(58) Field of Search .................................. 526/238.23

(56) References Cited

U.S. PATENT DOCUMENTS

| | | | |
|---|---|---|---|
| 4,070,348 A | | 1/1978 | Kraemer et al. ..... 260/79.3 MU |
| 4,503,174 A | * | 3/1985 | Vasta ........................ 523/439 |
| 5,089,106 A | | 2/1992 | Karger et al. ............ 204/299 R |
| 5,089,111 A | | 2/1992 | Zhu et al. ................. 204/180.1 |
| 5,134,187 A | * | 7/1992 | Aihara ....................... 524/548 |
| 5,143,753 A | | 9/1992 | Novotny et al. ............. 427/299 |
| 5,162,471 A | * | 11/1992 | Norberg ..................... 526/266 |
| 5,219,924 A | * | 6/1993 | Shih ........................... 524/832 |
| 5,470,916 A | | 11/1995 | Righetti et al. .............. 525/296 |
| 5,491,182 A | * | 2/1996 | Key ............................. 523/206 |
| 5,567,292 A | | 10/1996 | Madabhushi et al. ........ 204/451 |
| 5,935,401 A | | 8/1999 | Amigo ........................ 204/454 |
| 6,042,710 A | | 2/2000 | Dubrow ...................... 204/454 |
| 6,056,860 A | * | 5/2000 | Amigo ........................ 204/454 |
| 6,074,542 A | | 6/2000 | Dolnik et al. ................ 204/454 |

FOREIGN PATENT DOCUMENTS

WO    WO 99/38840    8/1999

OTHER PUBLICATIONS

S. Hjerten, "High–Performance Electrophoresis Elimination of Electroendosmosis and Solute Adsorption", *Journal of Chromatography*, vol. 347, 1985, pp. 191–198.
M. Huang et al., "Evaluation of Surface–Bonded Polyethylene Glycol and Polyethylene Imine in Capillary Electrophoresis", *J. Microcolumn Separations*, vol. 4, 1992, pp. 135–143.
S. Hjerten, "A New Type of pH– and Detergent–Stable Coating for Elimination of Electroendosmosis and Adsorption in (Capillary) Electrophoresis", *Electrophoresis*, vol. 14, 1993, pp. 390–395.
C.L. Ng et al., "Prevention of Protein–Adsorption on Surfaces by Polyethylene Oxide–Polypropylene Oxide–Polyethylene Oxide Triblock Copolymers in Capillary Electrophoresis", *Journal of Chromatography A.*, vol. 659, 1994, pp. 427–434.
M. Gilges et al., "Capillary Zone Electrophoresis Separations of Basic and Acidic Proteins Using Poly(vinyl alcohol) Coatings in Fused Silica Capillaries", *Analytical Chemistry*, vol. 656, No. 13, Jul. 1, 1994, pp 2038–2046.
M.H.A. Busch et al., "Cellulose Acetate–Coated Fushed –Silica Capillaries for the Separation of Proteins by Capillary Zone Electrophoresis", *Journal of Chromatography A.*, vol. 695, 1995, pp. 287–296.

M. Huang et al., "Hydrolytically Stable Cellulos–Derivatives Coatings for Capillary Electrophoresis of Peptides, Proteins and Glycoconjugates", *Electrophoresis*, vol. 16, 1995, pp. 396–401.
M. Chiari et al., "Capillary Electrophoretic Separation of Proteins Using Stable, Hydrophilic Poly (acryloylamino–ethoxyethanol)–Coated Columns", *Journal of Chromatography A.*, vol. 717, 1995, pp. 1–13.
M. Chiari et al., "Synthesis and Characterization of Capillary Columns Coated with Glycoside–Bearing Polymer", *Analytical Chemistry*, vol. 68, No. 17, Sep. 1, 1996, pp. 2731–2736.
N. Iki et al., "Non–Bonded Poly(ethylene oxide) Polymer –Coated Column for Protein Separation By Capillary Electrophoresis", *Journal of Chromatography A.*, vol. 731, 1996, pp. 273–282.
A. Cifuentes et al., "Selectivity Change in the Separation of Proteins and Peptides by Capillary Electrophoresis Using High–Molecular–Mass Polyethyleneimine", *Journal of Chromatogrpahy B: Biomedical Applications*, vol. 681, pp. 21–27.
E. Simo–Alfonso et al., "Novel Acrylamido Monomers with Higher Hydrophilicity and Improved Hydrolytic Stability: I. Synthetic Route and Product Characterization", *Electrophoresis*, vol. 17, 1996, pp. 723–731.
Article titled "Coating Composition for Printed Paper and Manufacture" by T. Ikeda, et al., published in *6001 Chemical Abstracts* on Feb. 5, 1990, vol. 112, No. 6.

* cited by examiner

*Primary Examiner*—Paul R. Michl
(74) *Attorney, Agent, or Firm*—Thomas Schneck; David M. Schneck

(57) ABSTRACT

The instant invention describes uncharged water-soluble polymers to suppress electroosmotic flow in capillary electrophoresis. The polymers in the instant invention are copolymers of various derivatives of acrylamide and methacrylamide monomers with various glycidyl group containing monomers e.g., dimethylacrylamide and allyl glycidyl ether-epoxy poly(DMA)-, copolymers of various derivatives of acrylamide and methacrylamide with various allyl group containing carbohydrates and various glycidyl group containing monomers, such as allyl β-D-pyranoside (typically β-D-glucopyranoside) or allyl β-D-furanoside, allyl glycidyl ether-epoxy poly(AG-AA) and copolymers of four different monomers including various acryl and methacrylamide, various allyl group containing carbohydrates, various glycidyl group containing monomers and various diol group containing monomers, such as acrylamide, allyl β-D-pyranoside (typically β-D-galactopyranoside or N-allylgluconamide) or allyl β-D-furanoside, allyl glycydyl ether and allyoxy-1,2 propanediol-epoxy poly(AGal-AA-APD). The subject polymers adsorb onto the capillary surface, forming a highly hydrophilic, dynamic coating that suppresses electroosmotic flow. The subject polymers may be used as a coating prior to use of an electrophoresis microchannel or may be included in a separation media contained within the capillary column. The instant coatings and media are especially suitable for applications pertaining to the electrophoretic separation of various biomolecules, such as protein and DNA.

32 Claims, 9 Drawing Sheets

ROBUST POLYMER COATING

CROSS-REFERENCE TO RELATED APPLICATION

This application claims priority from U.S. provisional application Ser. No. 60/150,167, filed Aug. 21, 1999.

TECHNICAL FIELD

The instant invention pertains to polymers. In particular, the instant invention pertains to polymers, which are useful in capillary electrophoresis. Such polymers may be used as dynamic coatings for the inner surfaces of capillaries used for capillary electrophoresis and are also useful as media contained within such capillaries. The instant invention further pertains to a method for making such polymers and to a capillary containing such polymeric coatings and/or media.

BACKGROUND OF THE INVENTION

During the last decade, capillary electrophoresis (CE) has developed into a powerful analytical method due to its flexibility and low volume requirement. CE provides fast and efficient separations and offers the following advantages over conventional slab gel electrophoresis:

a) heat dissipation is very efficient in CE and Joule heating is minimized. This ensures negligible temperature gradients and thus reduces peak broadening. Due to these effects, strong electric fields (typically up to 400 V/cm) can be used, therefore reducing run time and diffusion, which again leads to smaller peak widths;

b) CE is compatible with a variety of detection methods, such as absorption, laser induced fluorescence (LIF), mass spectrometry, chemiluminescence, voltammetry etc. In the case of DNA separation, CE also offers full compatibility to existing biochemistry.

c) CE systems can inject directly from a variety of sample formats (e.g., Eppendorf tubes, microtitre plates, etc.) and even from single cells;

d) the separation process can be fully automated. Separation matrices and samples can be automatically injected, therefore avoiding the time consuming procedure of gel casting and sample loading;

e) multi-capillary devices offer the possibility to analyze samples in parallel.

Despite these positive features, room for improvement continues to exist in the area of CE. Improving the reproducibility of analysis times is of particular importance. Analyte effective mobility ($\mu_{eff}$) in CE is a constant value depending on buffer composition and temperature. On the other hand, apparent mobility is often less reproducible, as electroosmotic mobility ($\mu_{eo}$) can vary from run-to-run in a more a unpredictable way. Interaction of the analyte with the inner surface of the capillary contributes significantly to electroosmotic flow (EOF) variation. A number of CE applications, such as those involving the analysis of DNA and SDS-protein complexes, benefit from reduced EOF. For example, in the analysis of DNA, EOF suppression is required to prevent migration of the separation matrix out of the capillary and to avoid adsorption of protein contaminants and dyes to the capillary surface.

Several methods have been developed to control the surface properties of silica capillaries. Such methods include using a background electrolyte with suitable characteristics, dynamically coating the capillary surface with polymeric additives contained in the running buffer, and coating the capillary surface through covalent silanols derivatization. Although a number of different dynamic coatings produced by adsorption of a polymer from an aqueous solution have been described, a common problem of these coatings is that the polymer can be easily removed from the capillary wall simply by washing with water. Therefore, unless otherwise stabilized, these coating are efficient in suppressing EOF only when a small amount of polymer is dissolved in the running buffer and can replace the polymer removed by the water from the surface.

The difficulties associated with performing chemical derivatization on silica micro-channels represent a significant obstacle to the development of innovative techniques such as micro-chip technology. Multiple capillary array technology, where as much as 96 capillaries must be handled at a same time, requires very simple and reliable coating procedures. Accordingly, there exists a strong scientific and industrial interest in coating procedures that do not require the use of organic solvents, high viscous solutions, and elevated temperatures.

SUMMARY OF THE INVENTION

The instant invention relates to the use of uncharged water-soluble polymers to suppress electroosmotic flow in capillary electrophoresis. The subject polymers adsorb onto the capillary surface, forming a highly hydrophilic, dynamic coating which achieves EOF suppression without the addition of any polymer to the running buffer. The coatings of the invention possess an affinity for the capillary surface that may last for approximately 20 hours of continuous use, under an electric field in a running buffer containing 8M urea, at a pH 8.5 at 45° C. The subject polymers are also useful as separation media contained within the capillary column. The instant coatings and media are especially suitable for applications pertaining to the electrophoretic separation of various biomolecules, such as protein and DNA.

The polymers useful in the instant invention are copolymers of various derivatives of acrylamide and methacrylamide monomers with various glycidyl group containing monomers e.g.,. dimethylacrylamide and allyl glycidyl ether-epoxy poly(DMA)-, copolymers of various derivatives of acrylamide and methacrylamide with various allyl group containing carbohydrates and various glycidyl group containing monomers, such as allyl β-D-pyranoside (typically β-D-glucopyranoside) or allyl β-D-furanoside allyl glycidyl ether-epoxy poly(AG-AA) and copolymers of four different monomers including various acryl and methacrylamide, various allyl group containing carbohydrates, various glycidyl group containing monomer and various diol group containing monomer, such as acrylamide, allyl β-D-pyranoside (typically β-D-galactopyranoside or N-allylgluconamide) or allyl β-D-furanoside, allyl glycydyl ether and allyoxy-1,2 propanediol-epoxy poly(AGal-AA-APD).

The instant invention also pertains to a capillary coated and/or filled with the above polymers and to a method for separating biomolecules using such a capillary.

BEST MODE FOR CARRYING OUT THE INVENTION

Figure 1:
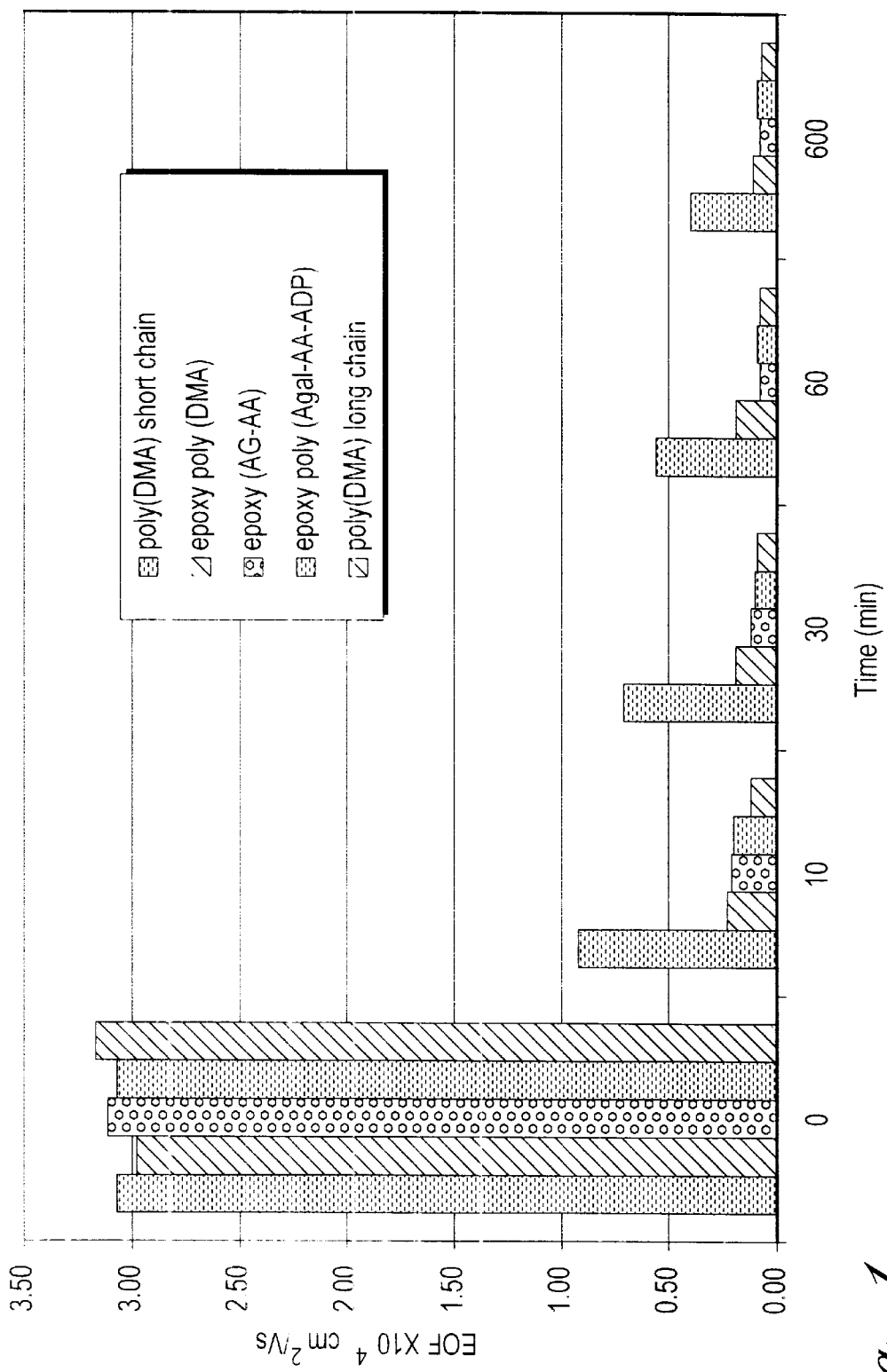
FIG. 1 shows the effect of coating time on the stability of various polymer coatings. Fifty μm capillaries were pretreated as described in Example 3 and equilibrated for different amounts of time (from 10 to 600 min.) with 0.1% (w/v) solutions of the various polymers.

The invention deals with the use of neutral polymers
1) to suppress electroosmotic flow and wall-analyte interactions in the separation of biomolecules by capillary and microchip electrophoresis and
2) as DNA sieving matrix for single and double stranded DNA molecules by capillary and micro-chip electrophoresis.

Concerning the use of the above mentioned polymers to suppress EOF, the polymers of the invention are co-polymers of various composition bearing oxyrane groups pending from the backbone. The polymers are obtained by radical polymerization of monomers in water catalyzed by ammonium persulfate and TEMED.

The copolymers contain two different monomeric units, such as: dimethylacrylamide and allyl glycidyl ether. Alternatively, the copolymers may contain three or more different monomeric units (e.g. acrylamide, an allyl monosaccharide (glucopyranoside or galactopyranoside or an allyl β-D-furanoside or N-allyl gluconamide) and allyl glycidyl ether; or four polymerized monomers (e.g. acrylamide, allyl monosaccharide, allyl glycidyl ether and allyoxy-1,2 propanediol). Their co-monomer composition (see Table 1, below) has been optimized to increase adsorption properties.

Poly (DMA) can be produced with chains of different sizes by carrying out the polymerization process in the presence or in the absence of a chain transfer agent, such as isopropanol. Our studies on the adsorbing properties of these polymers indicate that polymer length is a crucial parameter to achieve a capillary coating stable over time. Our data indicate that long chain poly (DMA) produced in the absence of a chain transfer agent possess better adsorbing properties than any other polymer. This might depend on the fact that water is a poorer solvent for poly (DMA) than for other more hydrophilic polymers, but also on the fact that the structure of this polymer is such that it form a higher number of hydrogen bridges with adsorptive sites on the silica. However, although useful in many applications, hydrophobic coatings are not recommended for proteins. In a previous work we demonstrated that most proteins possess hydrophobic patches that interact with hydrophobic polymers and which can have has dramatic consequences on separation efficiency and reproducibility (Chiari et al., *Anal. Chem.*, 68 (1996) 2731). The effects on peak profiles caused by interaction are similar to those due the presence of unmasked silanols or, more generally, to the presence of immobilized charges. In an attempt to conjugate adsorbing properties with hydrophilicity, the present invention proposes to synthesize highly hydrophilic polymers consisting of an alkyl backbone bearing oxyrane and/or glucose units. Epoxy groups pendent from the polymer backbone dramatically improve adsorption leading to the possibility of using the dynamically coated capillaries in the absence of any polymer added to the background electrolyte (BGE). The reason why such a small amount of oxyrane substituent changes polymer properties in such a dramatic way is probably the occurrence of a hydrogen bonding (secondary interaction) between wall silanols and polymer oxyrane groups. Oxyrane groups have limited hydrolytic stability, but even their hydrolysis-byproduct (diols) are prone to form hydrogen bonding with the wall silanol groups. As a result, the adsorptive properties of these polymers remain excellent. The oxyrane groups can also cause cross-linking of the contiguous chains bearing sugar hydroxyl groups, which can also increase the stability of the adsorptive coating; however, it can also cause insolubility problems during long term storage of the polymer.

In accordance with one embodiment of the instant invention, an amount of polymer ranging from 0.001 to 2% (w/v), typically 0.1% (w/v), is dissolved in water or in an aqueous medium of high ionic strength such as sodium phosphate, ammonium sulfate, sodium chloride. The polymer is then adsorbed to the silica surface from the solution described above, resulting in a viscosity increase of the liquid near the electric double layer without affecting bulk viscosity. The polymer may be coated onto the capillary (or similar microchannel such as a in a chip-like substrate) and the capillary then used for electrophoresis procedures. The coating is sufficiently stable that it does not need to be refreshed prior to each electrophoretic separation. Alternatively, the polymer may also be included within the separation media (e.g. separation matrix). In the separation media, the polymer is included at a concentration ranging from 0.001 to 10% (w/v). In some applications, the polymer may be used alone as the sieving matrix. The polymer may be included in all of the separation media, or may be used only in the first one or two electrophoretic separation. The coating from these few separations will be retained for a hundred or more separations. The coating polymer may be included in the separation media after a hundred or more separations, effectively recoating the capillary. After one or a few sequencing runs using a separation media including the polymer coating, the capillary is effectively recoated and may be reused again for more than one hundred separations. The adsorptive capillary coating is performed in a time variable from 10 min to 24 hour from an aqueous solution, at room temperature, and reduces EOF below a value of 0.2 $10^{-8}$ cm$^2$/Vs. EOF is measured in 20 mM Bicine-Tris buffer, pH 8.5.

Using aqueous medium with high ionic strength to prepare the coating polymer solution changes the surface properties of the coated capillary dramatically. This could be due to a different polymer conformation in the coating solution when salt is added, leading to a prevalence of hydrophobic interactions with the wall with exposure of hydrophilic functionality towards the capillary channel.

Adsorption of the polymers of the invention to the capillary wall occurs within 10 minutes. The degree of adsorption was measured indirectly by observing the reduction of EOF under a set of specified conditions. EOF was measured in 25 mM Bicine-Tris buffer, pH 8.5, 25° C., capillary 50 or 75 $\mu$m ID, by a method that provides accelerated electroosmosis measurements in capillary electrophoresis recently reported by Williams and Vigh (*Anal. Chem.*, 68, 1996, 1174–1180). Under the above reported conditions, the polymers of the invention are able to suppress EOF down to a value of 0.2 $10^{-4}$ cm$^2$/Vs.

The different coatings produced by the polymers of the invention can be used in various alkaline buffers (such as TAPS-TRIS EDTA, 8M urea, pH 8.5) with and without the use of a sieving matrix (such as linear polyacrylamide), at temperatures up to at least 45° C., for at least 30 hours without addition of polymer to the running buffer. To the best of our knowledge, all presently known adsorbed coatings for capillary electrophoresist unless otherwise stabilized, operate with addition of polymer to the background electrolyte (BGE) to avoid polymer displacement from the wall surface by water molecules with the exception of poly(ethylene) oxide (Iki and Yeung, *Journal of Chromatography A*, 731, 1996, 273–282). However, the coating procedure based on this polymer requires coating the capillary before each run; its effectiveness at pH higher than 7 was not demonstrated and no data were provided on stability of the adsorbed coating. All the other methods, which are based on the adsorption of non-ionic polymers, require special techniques such as silanized columns, thermal treatments or organic solvents and evaporation (Gilges, Kleemiss and Shomburg, *Anal. Chem.*, 66 (1995) 287; Busch, Kraak and Poppe, *J. Chromatogr. A.*, 695 (1995) 287; Ng, Lee, Li, *J. Chromatogr A.*, 659 (1994) 427.

The instant polymers may also be used as separation media and packed inside the coated or un-coated capillary column using commonly known packing techniques. In particular, one of the monomer used to produce the various copolymers, the allyl glycidyl ether, contains masked hydroxyl functions. Its presence in co-polymers that do not contain other hydroxyl groups strongly improves their hydrophilic properties. By acid or base catalyzed hydrolysis of the epoxy functionality, pending from the polymer backbone, hydroxyl groups are produced. Generation of hydroxyl groups from epoxide groups is advantageous over the directed polymerization of monomers bearing hydroxyl functionality as the latter groups are known to have chain transfer activity in radical polymerization, resulting short polymer chain formation. It is well known that the molecular weight of a polymer plays a crucial role in its sieving properties, particularly in DNA sequencing. Introducing epoxy groups onto a polymer chain not only increases the adsorptive and hydrophilic properties of the polymer, but also introduces functional groups that can potentially generate hydroxyl functionality after the polymerization is completed (without inhibiting polymer growth). Epoxy monomers have been selected, as an example amongst different functional groups able to generate hydrophilic groups by hydrolysis. Hydrolyzed epoxy poly(DMA) with a $M_w$ of 3 M kDa, for instance, can be used in CE as DNA sieving matrix for DNA in an un-coated capillaries. Its sieving capability differs significantly from those of a poly (DMA) with the same molecular mass as it will be shown in one of the examples.

Copolymers of dimethylacrylamide and allylglycidil ether (or the hydrolyzed diol of this compound) may be generated by incubating a capillary or other microchannel with a polymer solution containing 0.05 to 0.5% w/v of the polymer solution. The resulting coated capillary may be used for hundreds of sequencing runs without either recoating or including the polymer in the separation media (e.g. separation matrix). The polymer has a unique affinity for silica surfaces such that the polymer does not need to be included in the separation matrix.

The copolymers of the present invention include copolymers of dimethylacrylamide (DMA) and a second copolymerized monomer, the copolymer being more hydrophillic than dimethylacrylamide. The dynamic coating may include a copolymer of dimethylacrylamide and at least a second copolymerized monomer, the second copolymerized monomer making the copolymer less hydrophobic than poly (dimethylacrylamide). It is believed that other polymers such as polyethyleneoxide, polyvinylpirolidone, N,N-alkylsubstituted acrylamides, may also be used as dynamic coating in accordance with the present invention.

Various combinations of polymers may be used as coatings and separation media to optimize the separation and EOF conditions for particular applications. Capillaries coated with the instant polymers and/or packed with the instant polymers as separation media are suitable for separation of charged molecules, especially large biomolecules such as protein and DNA. The following examples are for illustration purposes only and should not be used in any way to limit the appended claims.

EXAMPLE 1

Synthesis of Poly (DMA)

Linear poly(DMA) of different relative molecular mass, Mw 230,000, and Mw 3,000,000 is synthesized using conventional techniques. Poly(DMA) of reduced chain length is synthesized using 2-propanol as a chain transfer agent to control the molecular mass of the product. A solution of freshly distilled N,N-dimethyl acrylamide (1 g) is dissolved in 9.7 mL of water and degassed under vacuum for 30 min. Isopropanol (0.3 mL) is then added to the reaction vessel. Next, 100 $\mu$L of 10% (v/v) N,N,N',N'-tetramethylethylendiamine (TEMED) in water and 10 $\mu$L of a 40% (w/v) ammonium persulfate in water is added. The mixture is allowed to react for 1 hour at 50° C. To remove any unreacted monomer and contaminants, the reaction mixture is dialyzed against water using a 12000 molecular mass cut-off dialysis membrane from Sigma. The solution is lyophilized to give 0.8 g of a white solid. A similar procedure is adopted to produce long-chain poly(DMA) in the absence of isopropanol. The average molecular masses (Mw) of the different polymers are determined by GPC-LS.

The polymer samples were dissolved in a solution containing 0.1 M NaNO$_3$ and 0.05% NaN$_3$ at a concentration of 2 g/l. For analysis, 50 uL polymer samples were injected into Waters Alliance system (Milford, Mass.) to fractionate the polymer by SEC using Ultrahydrogel 2000 column (Milford, Mass.) with the mobile phase containing 0.1 M NaNO₃ and 0.05% NaN₃ at flow rate 0.5 mL/min. The polymer zones were detected with on-line multi-angle laser light scattering (MALLS) detector Dawn (Wyatt Technology, Santa Barbara, Calif.) and refractive index (RI) detector Waters 2410 (Milford, Mass.). The signal from RI detector was used to determine the polymer concentration in each slice of chromatogram using the value of dndc being of 0.147 ml/mg as determined separately. The MALLS data were processed using ASTRA software (Wyatt Technology, Santa Barbara, Calif.).

EXAMPLE 2

Synthesis of Polymers Bearing Oxyrane Groups

All polymerization reactions are carried out in a two-necked, round-bottomed flask equipped with nitrogen inlet tube, and addition funnel. The designated amount of monomers (Table I) are dissolved in distilled water and then, after purging with purified $N_2$ gas, solutions of TEMED (0.14% v/v) and ammonium persulfate (0.05% w/v) are added to catalyze the reaction. The mixture is allowed to polymerize overnight at room temperature. Epoxy poly AG-AA is then precipitated by adding methanol to the solution whereas epoxy poly(DMA) is directly dialyzed against water. To remove any unreacted monomer and contaminants, the polymers are re-dissolved in water and dialyzed against water using a 12000 molecular mass cut-off dialysis membrane from Sigma. The solutions are lyophilized to produce white solids.

TABLE 1

Monomer composition of polymerization solutions used for the different copolymers

| POLYMER | AA mll/L | DMA mol/L | AG mol/L | AGal Mmol/L | APD mol/L | AE mol/L |
|---|---|---|---|---|---|---|
| Epoxy poly (AGal-AA-APD) | 1.69 | — | — | 0.42 | 0.24 | 0.122 |
| Epoxy poly (AG-AA) | 1.40 | — | 0.63 | — | — | 0.005 |
| Epoxy poly DMA | — | 0.4 | — | — | — | 0.008 |

Wherein:
AA=acrylamide
AG=allyl β-D-glucopyranoside
Agal=allyl β-D-galactopyranoside
AE=allyl glycidyl ether
DMA=dimethylacrylamide
APD=allyoxy-1,2 propanediol

EXAMPLE 3

Coating Procedure

Capillary Pre-treatment: Fifty μm I.D. capillaries are first pretreated with 0.1 M NaOH for a period of time ranging from 10 minutes to 1 hour, followed by 5–45 minutes of washing with deionized water.

Dynamic adsorption of linear polymer: A 0.1% (w/v) solution of the polymers in DI water or in an appropriate salt solution, unless otherwise specified, is forced for 10 minutes to 2 hours through the capillary, at room temperature, under a nitrogen pressure of 3 atm. The solution is allowed to remain in the capillary for 10 minutes to 12 hours (typically 10 min) and subsequently removed by washing the capillary with water under a nitrogen pressure of 3 atm.

Capillary regeneration: The coating is regenerated by washing the capillary with 0.1 M NaOH solution for 10 minutes followed by the dynamic adsorption of the polymers as reported above.

EXAMPLE 4

Coating Kinetic

The time required to generate a dynamic coating onto the capillary surface is investigated by treating the capillaries as reported in Example 3. A 0.1% (w/v) solution of the different polymers in deionized water is allowed to remain in the capillary for an amount of time varying from 10 to 600 minutes. Afterwards, the capillaries are emptied as reported in Example 3 and the EOF measured in 20 mM Bicine-tris buffer, pH 8.5 as reported above.

FIG. 1 shows the dependency of EOF from the time of contact between the polymer and the surface. As clearly illustrated by the figure, with the exception of short chain poly (DMA), a significant reduction of EOF is achieved in only 10 min. A further period of contact does not lead to any significant suppression.

EXAMPLE 5

Degradation Kinetic of Dynamically Coated Capillaries

Figure 2:
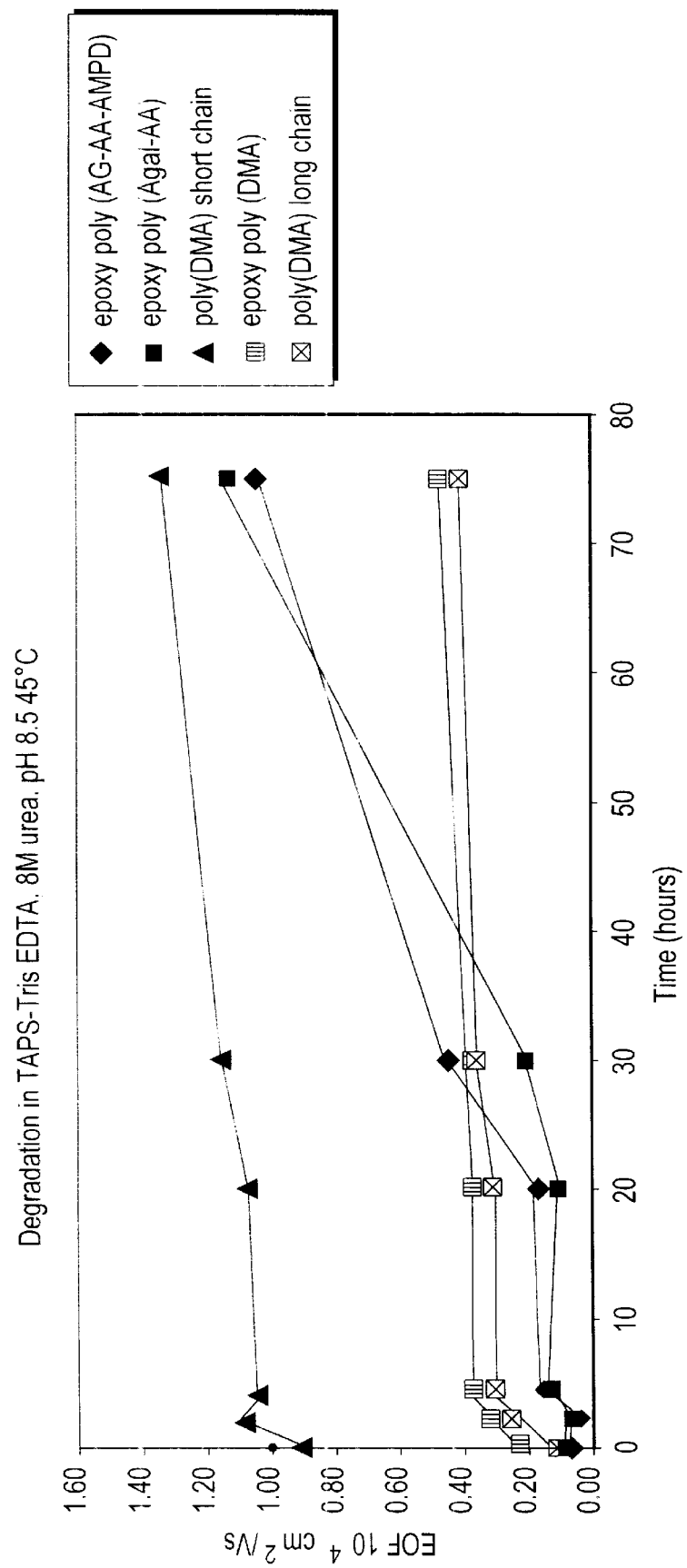
FIG. 2 shows the degradation over time of capillaries coated by dynamic adsorption of various polymers in TAPS- TRIS, EDTA, 8 M urea solution at pH 8.5 and 45° C. The capillaries were coated by flushing the polymer solution within the capillary column for 10 minutes.
Figure 3:
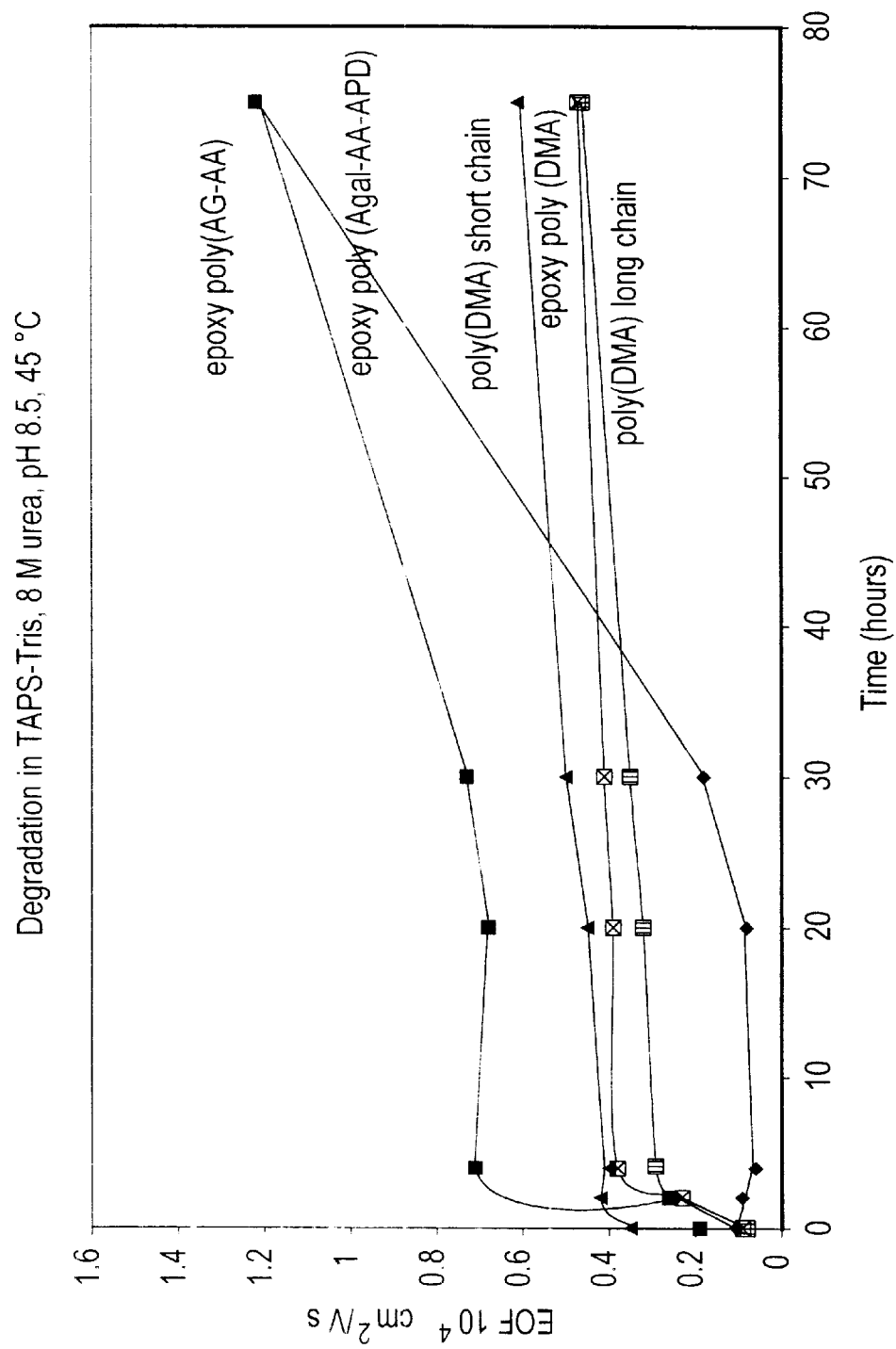
FIG. 3 shows the degradation over time of capillaries coated by dynamic adsorption of the same polymers shown in FIG. 2 above in TAPS-Tris, EDTA, 8 M urea solution at pH 8.5 and 45° C. The capillaries were coated by flushing the polymer solution within the capillary column for 10 minutes followed by 24 hours of contact between the capillary surface and the polymer.

Two series of capillaries are coated as described in Example 3. The first series of capillaries are coated with polymers for 10 minutes. The second series of capillaries are coated for 24 hours. The capillaries are subjected to degradation under conditions similar to those currently used in DNA sequencing: 100 mM TAPS-TRIS, EDTA buffer, 8 M urea and 45° C. The aim of this experiment is to investigate whether the stability of coatings produced by dynamic adsorption in 10 minutes is comparable to coatings produced by equilibrating the surface with the polymer solution for 24 hours. As shown in FIGS. 2 and 3, the lifetime of epoxy poly (DMA) and long chain poly (DMA) is very similar and longer than that of polymers containing hydroxyl functions. FIGS. 2 and 3 also show that there are no differences in the stability depending on contact time between polymer and surfaces, except for short chain poly (DMA) and epoxy poly (AG-AA).

EXAMPLE 6

Figure 4:
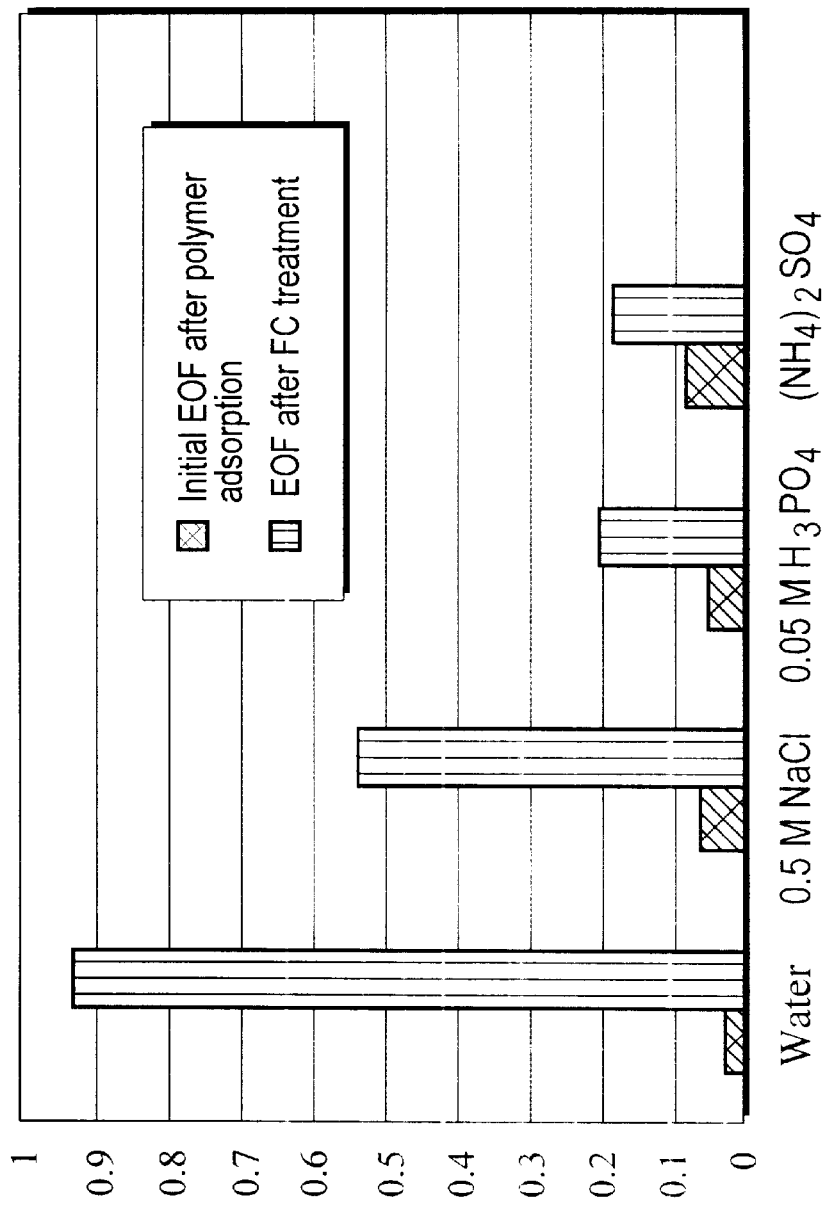
FIG. 4 reports EOF after washing the capillaries produced by adsorption of epoxy poly(DMA) from solution of different salts with a 1 mM solution of an anionic detergent, the FC129.

Dependence of Surface Properties on Ionic Strength of the Coating Polymer Solution The effect of various salts in the coating polymer solution on the properties of the coated capillary is investigated by measuring the EOF after a wash of the capillary with a hydrophobic, anionic detergent, the N-Ethyl-N-[(heptadecafluorooctyl)-sulfonyl]glycine (FC129). The EOF of the adsorbed-coated capillaries is measured before and after washing the capillary with a 1 mM solution of the FC129, for 5 min by applying a pressure of 15 psi. Since the detergent is negatively charged, when it adsorbs to the surface, due to hydrophobic interaction, it will result EOF generation on the originally neutral coated wall surface. A 45 cm long, 50 μm ID capillary is dynamically coated with epoxypoly(DMA) using the conditions described in Example 3 with the only difference that the polymer, during the adsorption step, was dissolved in different salt solutions such as 0.5 M sodium chloride, 0.05 M sodium phosphate, 0.9 M ammonium sulfate. As shown in FIG. 4, the addition of different salts decreased the detergent adsorption, thus improved the hydrophilicity of the coating dramatically. This example suggests the possibility to tune the properties of any amphiphilic-adsorbed polymer from hydrophobic to more hydrophilic by plying on the polymer conformation in the coating solution.

EXAMPLE 7

Figure 5:
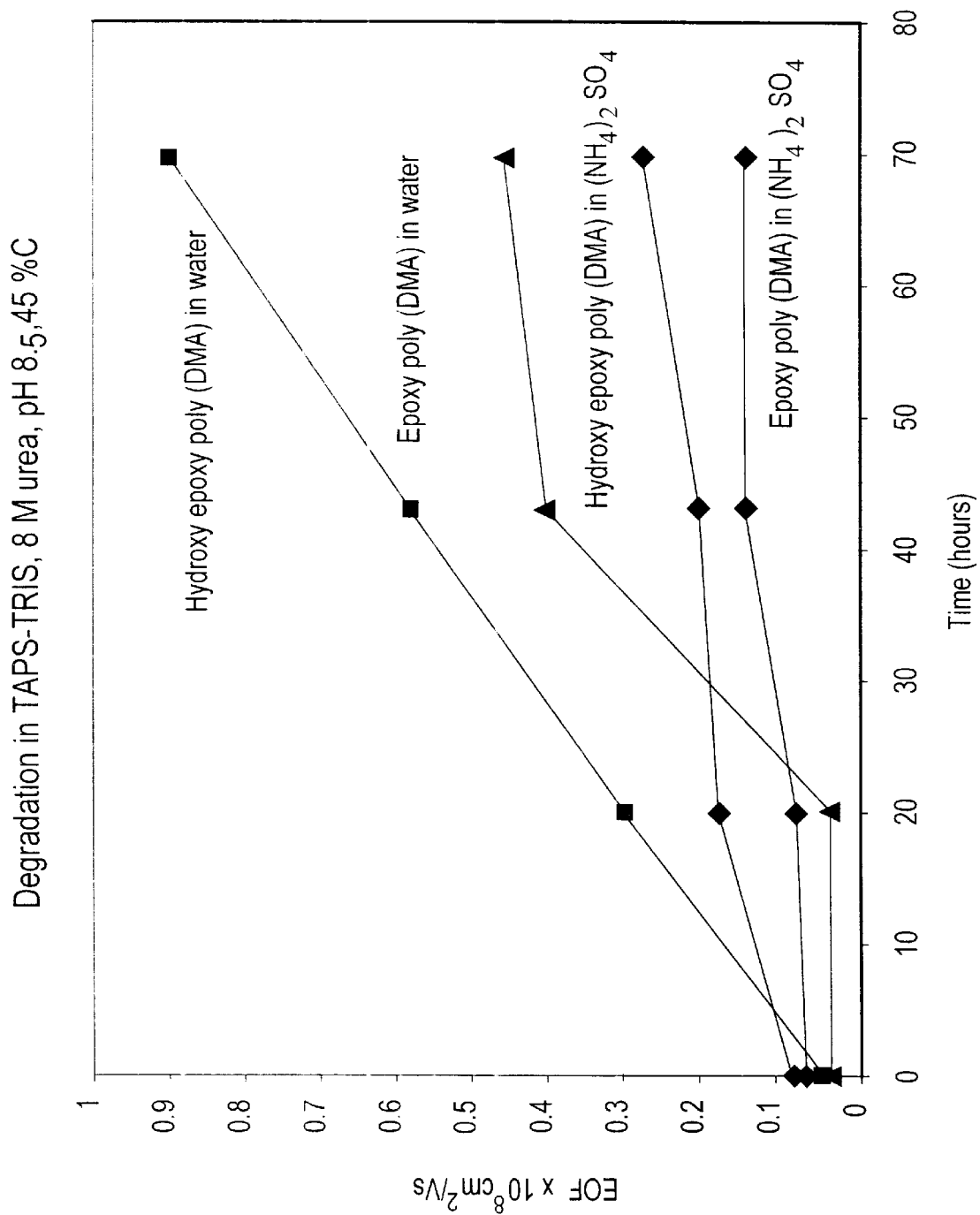
FIG. 5 shows the degradation of epoxy-poly-DMA and hydrolyzed epoxy-poly-DMA coated capillaries in TAPS-Tris, EDTA, 8 M urea solution at pH 8.5 and 45° C. The capillaries were coated by flushing the capillary column for 10 minutes with the polymer solution prepared with DI water and with 0.92M ammonium sulfate.

Stability of Adsorbed Coatings as a Function of the Composition of Polymer Adsorbing Solution Two-two capillaries, coated as reported in example 3 with the epoxy poly(DMA) and hydrolyzed epoxy poly(DMA) polymers dissolved in water or in 0.92 M ammonium sulfate are subjected to degradation under conditions similar to those currently used in DNA sequencing: 100 mM TAPS-TRIS, EDTA buffer, 8 M urea and 45° C. The aim of this experiment is to investigate whether the stability of the coatings produced by dynamic adsorption from different ionic strength solutions is similar. As shown in FIG. 5, the EOF of both epoxy poly (DMA) and hydrolyzed epoxy poly (DMA) adsorbed from ammonium sulfate solution is lower than that of the same polymer adsorbed from water.

EXAMPLE 8

Figure 6:
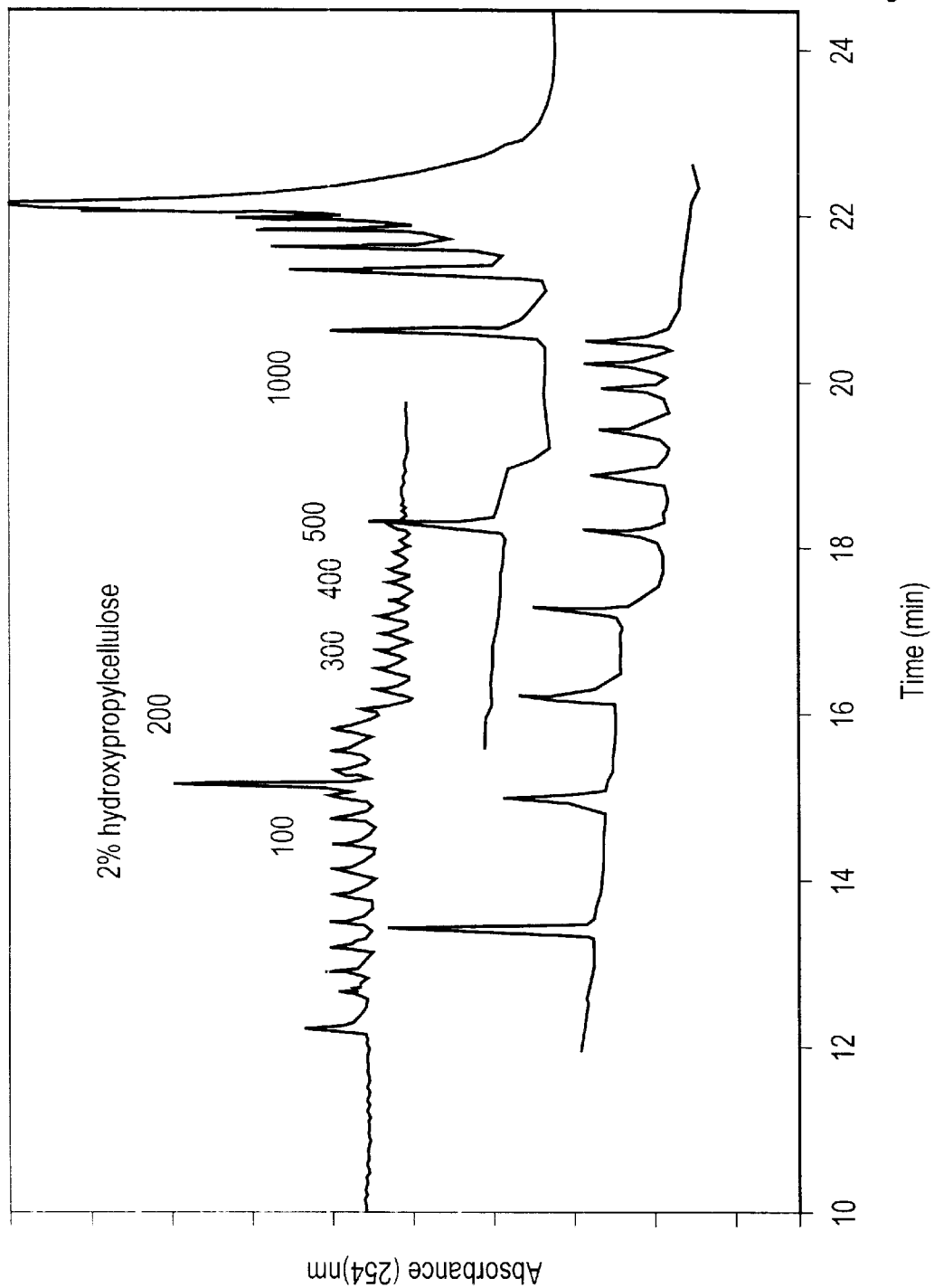
FIG. 6 shows the electrophoretic separation of DNA ladders of various sizes in an epoxy-poly-DMA coated capillary using hydroxypropyl cellulose as a sieving matrix.

Electrophoretic Separations of Various DNA Samples in Dynamically Coated Capillaries A 45 cm long, 75 um capillary is dynamically coated with epoxy-poly (DMA) polymer, using the conditions described in Example 3. DNA ladder standards of various sizes are separated in Taps-Tris-EDTA 100 mM running buffer, at pH 8.5, using 1.5% (w/v) hydroxyethyl cellulose (from Hewlett Packard) as sieving matrix. The applied voltage was −8 kV. The results shown in FIG. 6 illustrate the feasibility of using the instant dynamic coated capillaries for electrophoresis of DNA samples in combination with other polymer used as DNA sieving matrix.

EXAMPLE 9

Acidic Hydrolysis of Epoxy Poly (DMA)

Thirty mL of epoxy poly (DMA) polymer solution, synthesized as reported in Example 2, were added without further purification to 120 mL of 1.25 M sulfuric acid solution previously warmed at 60° C. After addition the composition of the solution is 0.8 w/v polymer in 1M sulfuric acid. The reaction mixture is gently stirred for 6 hours while maintaining the temperature at 60°. At the end of the reaction the polymer is purified by dialysis as reported in Example 3.

EXAMPLE 10

Figure 7:
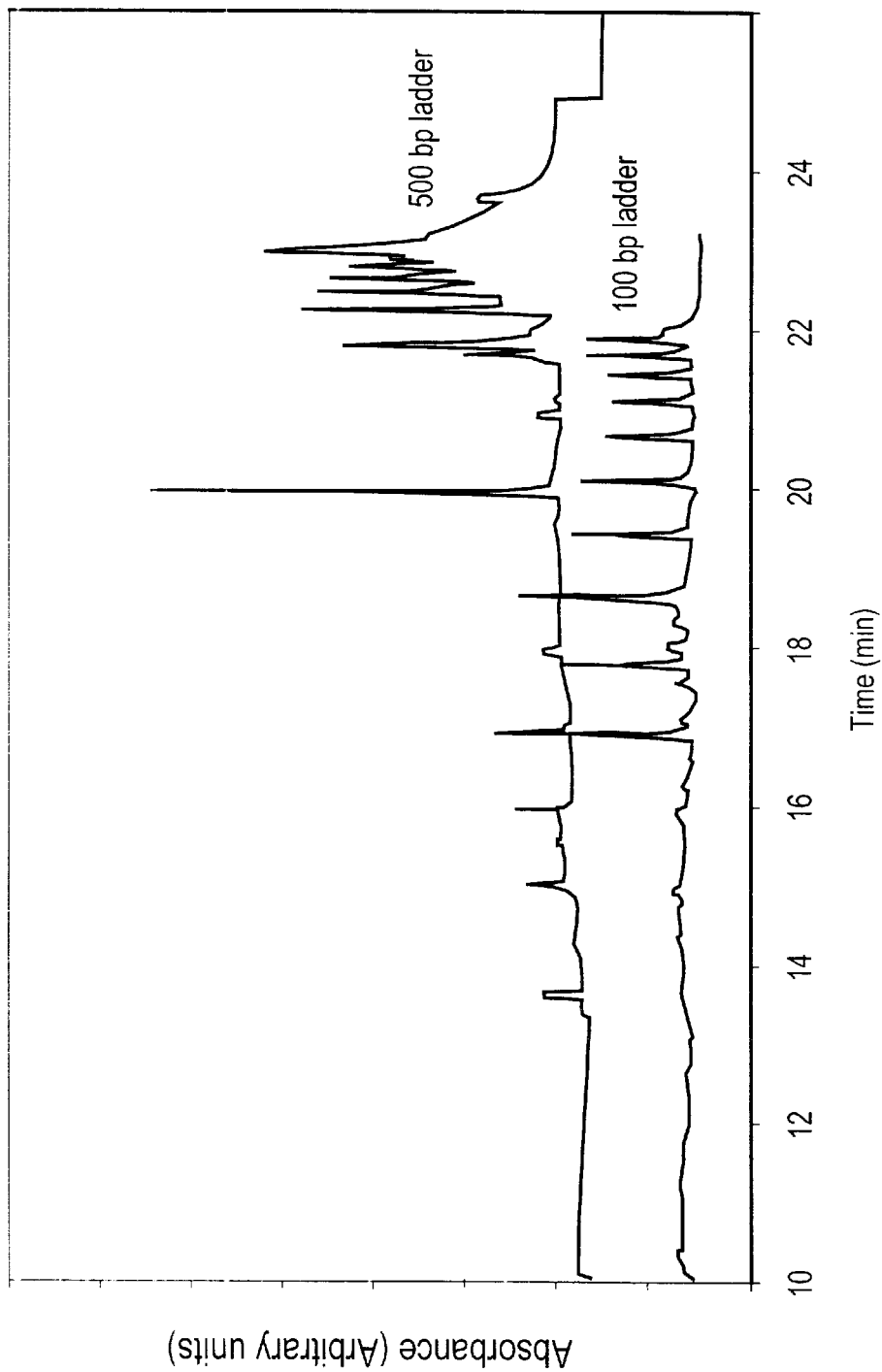
FIG. 7 shows the electrophoretic separation of DNA ladders of various sizes in an epoxy-poly-DMA coated capillary using hydrolyzed epoxy-poly-DMA as a sieving matrix.

Electrophoretic Separations of Various DNA Samples in Using Hydrolyzed Epoxy Poly(DMA) as the Sieving Matrix in an Epoxy Poly(DMA) Adsorbed Coated Capillary A 45 cm long, 75 um ID capillary is dynamically coated with epoxy-poly (DMA) polymer, using the conditions described in Example 3. DNA ladder standards of various sizes are separated in Taps-Tris-EDTA 100 mM running buffer, at pH 8.5, using 2% (w/v) hydrolyzed epoxy poly-DMA as sieving matrix. The applied voltage was −8 kV. The result, shown in FIG. 7, illustrate the feasibility of using the hydrolyzed epoxy poly(DMA) as the DNA separation matrix for DNA electrophoresis.

EXAMPLE 11

Figure 8:
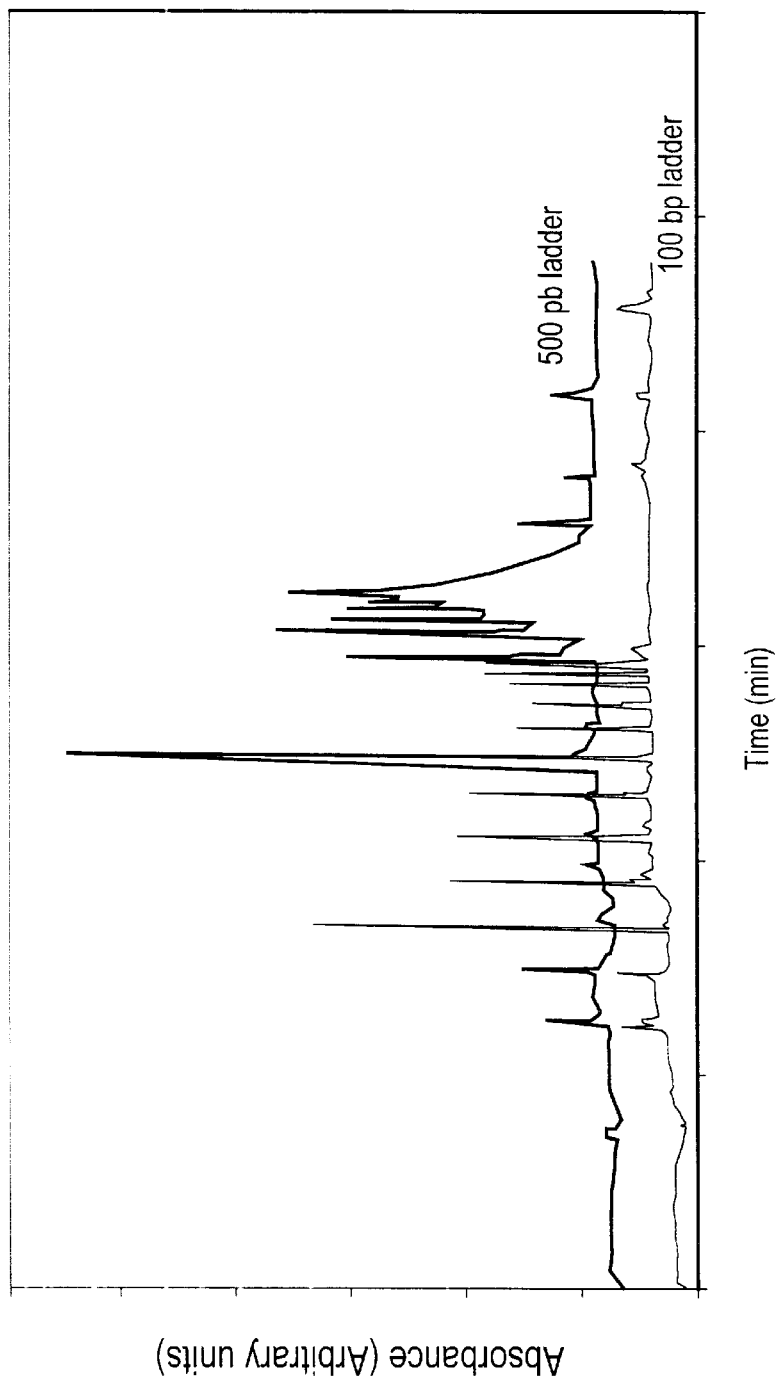
FIG. 8 shows the electrophoretic separation of DNA ladders of various sizes in an un-coated capillary using hydrolyzed epoxy-poly-DMA as a sieving matrix.

Electrophoretic Separations of Various DNA Samples in Using Hydrolyzed Epoxy Poly(DMA) as the Sieving Matrix in an Un-coated Capillary DNA ladder standards of various sizes are separated in a 45 cm long, 75 um ID fused silica capillary, filled with Taps-TRIS-EDTA 100 mM running buffer, at pH 8.5, using 2% (w/v) hydrolyzed epoxy poly(DMA) as the sieving matrix. The applied voltage was −8 kV. The results shown in FIG. 8 illustrate the feasibility of using the hydrolyzed epoxy poly(DMA) as the DNA separation matrix for DNA electrophoresis in an un-coated capillary. This result shows the self-adsorbing properties of the instant polymer onto the capillary wall.

EXAMPLE 12

Figure 9:
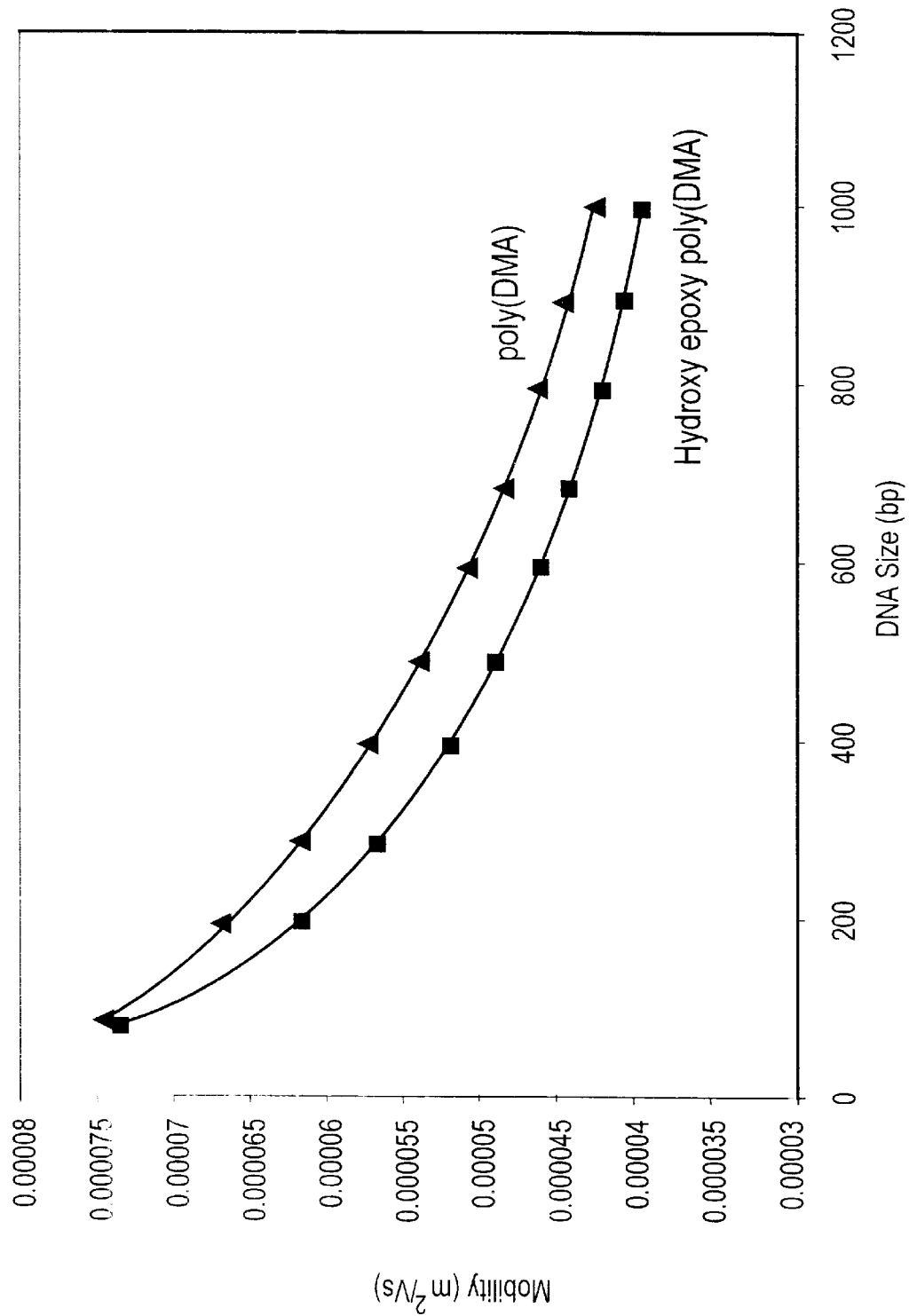
FIG. 9 compares the mobility of double stranded DNA fragments separated in poly(DMA) and hydrolyzed epoxy poly(DMA) in un-coated capillaries. The Mw of the two polymers is 3000 kDa.

Comparison of Electrophoretic Mobility of Double Stranded DNA Fragments in Poly(DMA) and Hydrolyzed Epoxy Poly(DMA) Ranging from 100 to 1000 bp The mobility versus the size of double stranded DNA fragments, in size range of 100 to 1000 bp, is reported in FIG. 9. The two curves refer to mobility data obtained in a 2% (w/v) poly(DMA) and hydrolyzed epoxy poly(DMA), both with Mw 3000 kDa, solution in 100 mM TAPS-TRIS, 2 mM EDTA buffer, pH 8.5. Separation conditions as in Example 8.

EXAMPLE 13

Preparation of Sieving Gel Containing Dynamic Coated Capillary Arrays for DNA Sequencing A capillary array, containing 16 individual (75 μm ID, 64 cm long (44 cm effective length)) capillaries is dynamically coated with epoxy-poly-DMA using the MegaBACE 1000™ DNA Sequencer from Molecular Dynamics. The arrays are first pretreated with 0.1 M NaOH for 15 minutes, followed by 2 high (1000 psi) and 2 low (400 psi) pressure washes with deionized water. A 0.1% (w/v) solution of the polymers is forced through the array by using two high-pressure (1,000 psi) fills for 5—5 seconds. The polymer solution is allowed to remain in the arrays for 10 minutes and subsequently removed by washing the array with deionized water, using two high (1,000 psi) and two low (400 psi) pressure rinse. The dynamic coated array is then rinsed with the background electrolyte (TAPS-TRIS, EDTA, 8 M urea solution at pH 8.5) using consecutive pressure rinses. The array is then filled with 0.3% linear polyacrylamide (LPA) gel matrix, using a 200 second high pressure rinse (1,000 psi), and allowed to equilibrate for 20 minutes. After the equilibration, a 5-minute pre-run is performed by applying 10 kV on the array.

EXAMPLE 14

DNA Sequencing Using Dynamically Coated Capillaries

A dynamic coated capillary array filled with background electrolyte (TAPS-Tris, EDTA, 8 M urea solution at pH 8.5) and linear polyacrylamide sieving gel matrix (0.3% w/v) is prepared as described in Example 13. A sample of DNA M13 in 70% formamide and 1 mM EDTA is injected at 5 kV for 40 seconds and sequenced using a MegaBace-1000™ DNA Sequencer. The separation voltage was 10 kV, the sequencing temperature was 45° C. Average read-lengths over 600 can be routinely achieved using dynamically coated capillary arrays.

EXAMPLE 15

Stability Study of Dynamically Coated Capillaries Under DNA Sequencing Conditions To study the stability of the non-covalently bonded arrays in DNA sequencing, consecutive DNA sequencing runs are performed using the same conditions as described in Example 14. The average readlength of the 16 capillary for each array is plotted in the function of the number of runs performed. After about 200 runs, the array is re-coated by repeating the array coating procedure described in example 13. The dynamic capillary coating is stable for over 200 consecutive sequencing runs (over 300 hours), without recoating of the capillary surface or without having polymer additive in the background electrolyte. After this time, a brief re-coating procedure can restore the original array performance. The performance of coated capillaries realized readlengths longer than 700 bases, with average readlengths above 500 bases for over 200 sequencing runs.

Although various embodiments of the instant invention are described in detail above, the instant invention is not limited to such specific examples. Various modifications will be readily apparent to one of ordinary skill in the art and fall within the spirit and scope of the following appended claims.

What is claimed is:

1. A dynamically coated microchannel comprising;
   a microchannel;
   a dynamic microchannel coating, said coating comprising at least one copolymer comprised of at least a first and a second copolymerized monomers, said first monomer selected from a group consisting of acrylamide, methacrylamide, N-monosubstituted acrylamide, N-monosubstituted methacrylamide, N,N-disubstituted acrylamide, and N,N-disubstituted methacrylamide; and said second monomer selected from the group consisting of glycidyl group containing monomers, diol group containing monomers and allyl group containing carbohydrate monomers.

2. The dynamically coated microchannel of claim 1, wherein the dynamic coating includes at least the first, the second, and a third copolymerized monomers, said third monomer being a diol group containing monomer.

3. The dynamically coated microchannel of claim 2, wherein the second monomer is an glycidyl group containing monomer and said copolymer includes a glycidyl containing monomer as a fourth copolymerized monomer.

4. The dynamically coated microchannel of claim 1, wherein the copolymer is selected from the group consisting of:
   a copolymer of acrylamide monomers, allyl glycidyl ether monomers, and allyl β-D-glucopyranoside monomers;
   a copolymer of dimethylacrylamide monomers and allyl glycidyl ether monomers;
   a copolymer of acrylamide monomers, allyl glycidyl ether monomers, and allyl β-D-galactopyranoside monomers;
   a copolymer of acrylamide monomers, allyl glycidyl ether monomers, and N-allyl gluconamide monomers;
   a copolymer of acrylamide monomers, allyl glycidyl ether monomers, allyl β-D-glucopyranoside monomers, and allyloxy-1,2-propanediol monomers;
   a copolymer of acrylamide monomers, allyl glycidyl ether monomers, allyl β-D-galactopyranoside monomers, and allyloxy-1,2-propanediol monomers;
   a coplymer of dimethylacrylamide monomers and allyloxy-1,2-propanediol monomers; and
   a copolymer of acrylamide monomers, allyl glycidyl ether monomers, N-allyl amide of gluconic acid monomers, and allyloxy-1,2-propanediol monomers.

5. The dynamically coated microchannel of claim 4, wherein epoxy groups on the allyl glycidyl ether have been opened to form a diol.

6. The dynamically coated microchannel of claim 1, wherein the copolymer of said coating is included within a separation media contained with said microchannel.

7. The dynamically coated microchannel of claim 6, wherein said copolymer is present in said separation media at a concentration of between 0.001 and 10% w/v.

8. A method to suppress electroendoosmosis, the method comprising:
   filling a microchannel with a liquid containing a dynamic copolymer adsorption agent, said copolymer comprising at least one copolymer comprised of at least a first and a second copolymerized monomers, said first monomer selected from a group consisting of acrylamide, methacrylamide, N-monosubstituted acrylamide, N-monosubstituted methacrylamide, N,N-disubstituted acrylamide, and N,N-disubstituted methacrylamide; and said second monomer selected from the group consisting of glycidyl group containing monomers, diol group containing monomers and allyl group containing carbohydrate monomers;
   adding sample containing biopolymers into one end of said microchannel; and
   introducing an electrical current through said channel such that the biopolymers are separated as the sample moves through the microchannel.

9. The method of claim 8 wherein the liquid comprises a separation media.

10. The method of claim 9 wherein the liquid contains the dynamic copolymer adsorption agent at a concentration of 0.001 to 10% w/v.

11. The method of claim 8, wherein the following adding the copolymer to the microchannel and before adding the sample, the method further includes incubating the copolymer within the microchannel for at least ten minutes.

12. The method of claim 8, wherein the dynamic copolymer adsorbtion agent includes at least the first, the second, and a third copolymerized monomers, said third monomer being a diol group containing monomer.

13. The method of claim 12, wherein the second monomer is an glycidyl group containing monomer and said copolymer includes a glycidyl containing monomer as a fourth copolymerized monomer.

14. The method of claim 8, wherein the copolymer is dissolved in an aqueous medium of high ionic strength.

15. The method of claim 8, wherein the dynamic copolymer adsorbtion agent is selected from the group consisting of:
   a copolymer of acrylamide monomers, allyl glycidyl ether monomers, and allyl β-D-glucopyranoside monomers;
   a copolymer of dimethylacrylamide monomers and allyl glycidyl ether monomers;
   a copolymer of acrylamide monomers, allyl glycidyl ether monomers, and allyl β-D-galactopyranoside monomers;
   a copolymer of acrylamide monomers, allyl glycidyl ether monomers, and N-allyl gluconamide monomers;

a copolymer of acrylamide monomers, allyl glycidyl ether monomers, allyl β-D-glucopyranoside monomers, and allyloxy-1,2-propanediol monomers;

a copolymer of acrylamide monomers, allyl glycidyl ether monomers, allyl β-D-galactopyranoside monomers, and allyloxy-1,2-propanediol monomers;

a coplymer of dimethylacrylamide monomers and allyloxy-1,2-propanediol monomers; and a copolymer of acrylamide monomers, allyl glycidyl ether monomers, N-allyl amide of gluconic acid monomers, and allyloxy-1,2-propanediol monomers.

16. The method of claim 8, wherein electroendoosmosis is reduced to a value below $0.2 \times 10^{-8}$ m$^2$/Vs.

17. A dynamically coated microchannel comprising;
a silica microchannel;
a dynamic microchannel coating, said coating comprising at least one copolymer comprised of at least a first and a second copolymerized monomers, said first monomer selected from a group consisting of acrylamide, methacrylamide, N-monosubstituted acrylamide, N-monosubstituted methacrylamide, N,N-disubstituted acrylamide, and N,N-disubstituted methacrylamide; and said second monomer selected from the group consisting of glycidyl group containing monomers, diol group containing monomers and allyl group containing carbohydrate monomers.

18. The dynamically coated microchannel of claim 17, wherein the dynamic coating includes at least the first, the second, and a third copolymerized monomers, said third monomer being a diol group containing monomer.

19. The dynamically coated microchannel of claim 18, wherein the second monomer is an glycidyl group containing monomer and said copolymer includes a glycidyl containing monomer as a fourth copolymerized monomer.

20. The dynamically coated microchannel of claim 17, wherein the copolymer is selected from the group consisting of:

a copolymer of acrylamide monomers, allyl glycidyl ether monomers, and allyl β-D-glucopyranoside monomers;

a copolymer of dimethylacrylamide monomers and allyl glycidyl ether monomers;

a copolymer of acrylamide monomers, allyl glycidyl ether monomers, and allyl β-D-galactopyranoside monomers;

a copolymer of acrylamide monomers, allyl glycidyl ether monomers, and N-allyl gluconamide monomers;

a copolymer of acrylamide monomers, allyl glycidyl ether monomers, allyl β-D-glucopyranoside monomers, and allyloxy-1,2-propanediol monomers;

a copolymer of acrylamide monomers, allyl glycidyl ether monomers, allyl β-D-galactopyranoside monomers, and allyloxy-1,2-propanediol monomers;

a copolymer of dimethylacrylamide monomers and allyloxy-1,2-propanediol monomers; and a copolymer of acrylamide monomers, allyl glycidyl ether monomers, N-allyl amide of gluconic acid monomers, and allyloxy-1,2-propanediol monomers.

21. The dynamically coated microchannel of claim 20, wherein epoxy groups on the allyl glycidyl ether have been opened to form a diol.

22. The dynamically coated microchannel of claim 17, wherein the copolymer of said coating is included within a separation media contained with said microchannel.

23. The dynamically coated microchannel of claim 22, wherein said copolymer is present in said separation media at a concentration of between 0.001 and 10% w/v.

24. A method to suppress electroendoosmosis, the method comprising:

filling a silica microchannel with a liquid containing a dynamic copolymer adsorption agent, said copolymer comprising at least one copolymer comprised of at least a first and a second copolymerized monomers, said first monomer selected from a group consisting of acrylamide, methacrylamide, N-monosubstituted acrylamide, N-monosubstituted methacrylamide, N,N-disubstituted acrylamide, and N,N-disubstituted methacrylamide; and said second monomer selected from the group consisting of glycidyl group containing monomers, diol group containing monomers and allyl group containing carbohydrate monomers;

adding sample containing biopolymers into one end of said microchannel; and introducing an electrical current through said channel such that the biopolymers are separated as the sample moves through the microchannel.

25. The method of claim 24 wherein the liquid comprises a separation media.

26. The method of claim 25 wherein the liquid contains the dynamic copolymer adsorption agent at a concentration of 0.001 to 10% w/v.

27. The method of claim 24, wherein the following adding the copolymer to the microchannel and before adding the sample, the method further includes incubating the copolymer within the microchannel for at least ten minutes.

28. The method of claim 24, wherein the dynamic copolymer adsorbtion agent includes at least the first, the second, and a third copolymerized monomers, said third monomer being a diol group containing monomer.

29. The method of claim 28, wherein the second monomer is an glycidyl group containing monomer and said copolymer includes a glycidyl containing monomer as a fourth copolymerized monomer.

30. The method of claim 24, wherein the copolymer is dissolved in an aqueous medium of high ionic strength.

31. The method of claim 24, wherein the dynamic copolymer adsorbtion agent is selected from the group consisting of:

a copolymer of acrylamide monomers, allyl glycidyl ether monomers, and allyl β-D-glucopyranoside monomers;

a copolymer of dimethylacrylamide monomers and allyl glycidyl ether monomers;

a copolymer of acrylamide monomers, allyl glycidyl ether monomers, and allyl β-D-galactopyranoside monomers;

a copolymer of acrylamide monomers, allyl glycidyl ether monomers, and N-allyl gluconamide monomers;

a copolymer of acrylamide monomers, allyl glycidyl ether monomers, allyl β-D-glucopyranoside monomers, and allyloxy-1,2-propanediol monomers;

a copolymer of acrylamide monomers, allyl glycidyl ether monomers, allyl β-D-galactopyranoside monomers, and allyloxy-1,2-propanediol monomers;

a coplymer of dimethylacrylamide monomers and allyloxy-1,2-propanediol monomers; and a copolymer of acrylamide monomers, allyl glycidyl ether monomers, N-allyl amide of gluconic acid monomers, and allyloxy-1,2-propanediol monomers.

32. The method of claim 24, wherein electroendoosmosis is reduced to a value below $0.2 \times 10^{-8}$ m$^2$/Vs.

* * * * *